United States Patent
Leira et al.

(10) Patent No.: US 12,036,384 B2
(45) Date of Patent: Jul. 16, 2024

(54) REPLICATION OR MITIGATION OF LOW FREQUENCY VIBRATION AND OTHER PHYSICAL FACTORS TO ENHANCE THE EFFECT OF THROMBOLYSIS ON PATIENTS WITH ISCHEMIC STROKE

(71) Applicant: University of Iowa Research Foundation, Iowa City, IA (US)

(72) Inventors: Enrique C. Leira, Iowa City, IA (US); Thomas Schnell, Iowa City, IA (US); Salam F. Rahmatalla, Iowa City, IA (US); Andrew A. Pieper, Iowa City, IA (US); Anil Chauhan, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 16/783,003

(22) Filed: Feb. 5, 2020

(65) Prior Publication Data

US 2020/0316289 A1 Oct. 8, 2020

Related U.S. Application Data

(60) Provisional application No. 62/801,456, filed on Feb. 5, 2019.

(51) Int. Cl.
*A61M 5/142* (2006.01)
*A61H 1/00* (2006.01)

(52) U.S. Cl.
CPC ............ *A61M 5/142* (2013.01); *A61H 1/001* (2013.01); *A61H 2201/5048* (2013.01); *A61H 2209/00* (2013.01); *A61M 2005/14208* (2013.01); *A61M 2202/07* (2013.01)

(58) Field of Classification Search
CPC .... A61H 2209/00; A61M 2005/14208; A61M 2202/07; A61M 5/142; A61M 2250/00; A61M 2202/00; A61M 2202/0007; A61M 2202/0064; A61M 2202/0078; A61N 7/00; A61N 2007/0004; A61N 2007/0039; A61B 2017/22081; A61B 2017/22082; A61B 2017/22084; A61B 2017/22088
See application file for complete search history.

(56) References Cited

U.S. PATENT DOCUMENTS

2010/0222723 A1* 9/2010 Hoffmann ................ A61N 7/00
601/107
2018/0221241 A1* 8/2018 McMurtry ........... A61G 10/023

FOREIGN PATENT DOCUMENTS

WO 2005023121 A1 3/2005

\* cited by examiner

*Primary Examiner* — Jason E Flick
(74) *Attorney, Agent, or Firm* — Dentons Davis Brown; Matthew Warner-Blankenship

(57) ABSTRACT

The disclosed apparatus, systems and methods relate to devices, systems and methods for improving thrombolysis via synergetic application of thrombolytics with physical factors, such as in acute ischemic stroke patients. Vibration in the low (0.5-120 Hz) frequency range is synergistic with tissue plasminogen activators (rtPA), significantly improving the effectiveness of thrombolysis without impairing blood brain barrier permeability. Administration of low frequency vibration combined with rtPA improve acute ischemic stroke outcomes.

19 Claims, 7 Drawing Sheets

Animal box with rtPA pumps

Mi2 Helicopter

Animal box inside Mi2

Vibration simulator

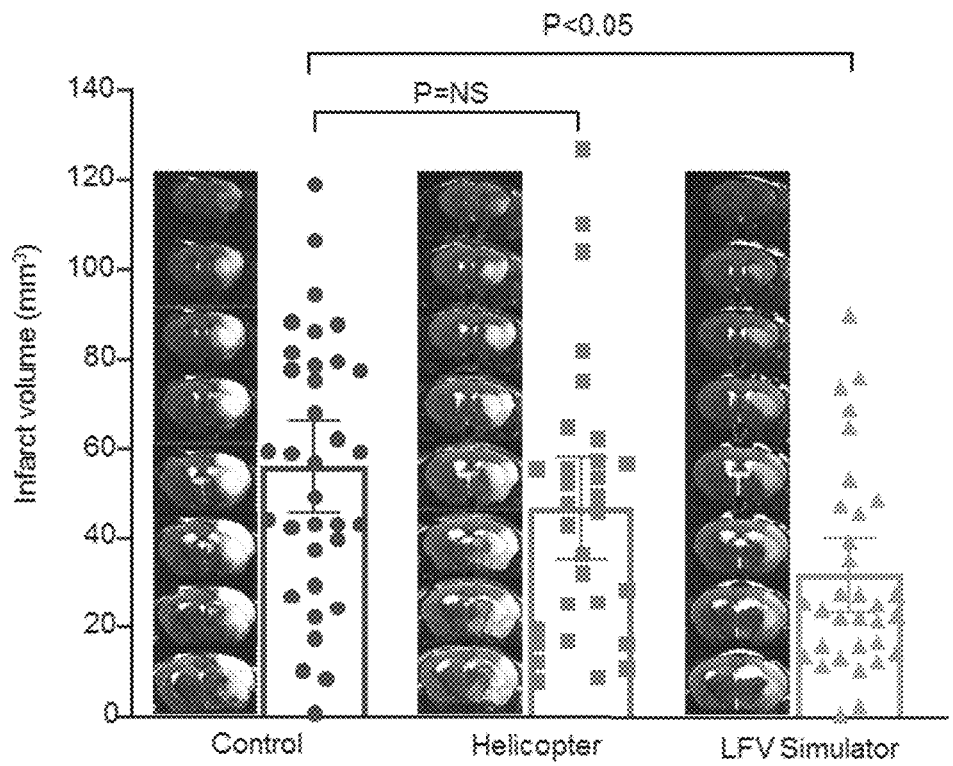
FIG. 7A
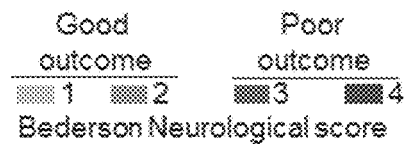
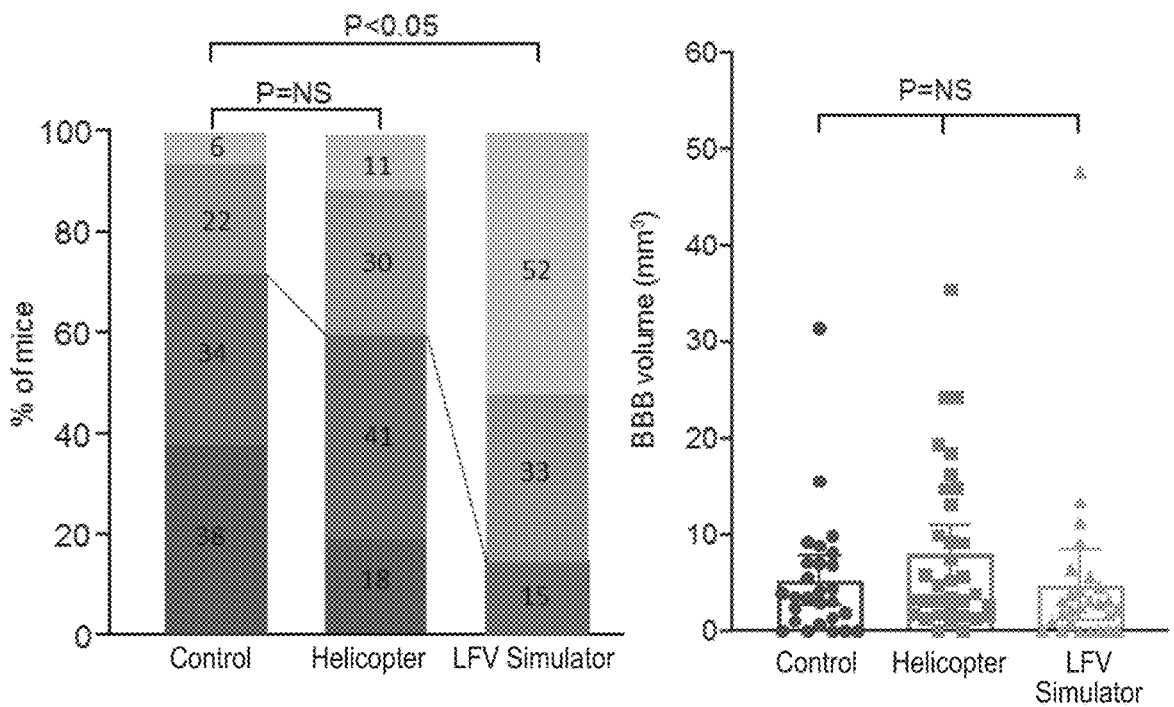
FIG. 7B    FIG. 7C

REPLICATION OR MITIGATION OF LOW FREQUENCY VIBRATION AND OTHER PHYSICAL FACTORS TO ENHANCE THE EFFECT OF THROMBOLYSIS ON PATIENTS WITH ISCHEMIC STROKE

CROSS-REFERENCE TO RELATED APPLICATIONS

This application claims priority to U.S. Provisional App. No. 62/801,456, filed Feb. 5, 2019 which is hereby incorporated by reference in its entirety under 35 U.S.C. § 119(e).

GOVERNMENT SUPPORT

This invention was made with Government support under Grant No. NS104579, awarded by the National Institutes of Health. The Government has certain rights to the invention.

BACKGROUND

The disclosure relates to apparatus, systems and methods for improved patient health outcomes. In various implementations, these apparatus, systems and methods relate to the treatment of stroke, brain injury and or other conditions that require helicopter emergent medical services (HEMS) transportation. The disclosure further relates to the treatment of patients that receive thrombolytics for the treatment of ischemic stroke. There is a need for interventions to improve the limited effectiveness of thrombolytics. HEMS is critical for rapid transportation of patients to centers capable of delivering mechanical thrombectomy while receiving thrombolytics. Some of the physical factors present in the helicopter flight, such as LFV, could have a positive effect on thrombolysis. There is a need to deliver neuroprotective agents in transportation to mitigate the effect of brain injury—such as ischemia—during helicopter and ground ambulance transport to improve the outcomes of patients living at a significant distance from a mechanical thrombectomy center.

However, the effect of the multiple unique physical factors present in HEMS on the outcomes of these procedures, thrombolysis and eventual neuroprotection, is not known. Experimental models of ischemia-reperfusion that accurately replicate HEMS conditions were developed in order to address this issue before putative neuroprotective therapies during flight trials can be accurately evaluated.

BRIEF SUMMARY

Discussed herein are various devices, systems and methods relating to novel methods of treatment for patients in need thereof via the application of physical forces. In various implementations, the patients or subjects are in need of thrombolytic treatment. In various implementations, vibrational forces are administered to the patients or subjects. An experimental "drip & ship" animal model was employed to study the effects of various forces present in the helicopter and isolate those forces for further analysis.

A system of one or more computers and devices can be configured to perform particular operations or actions required by the foregoing Examples by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In Example 1, a method of enhancing thrombolysis in a subject with acute ischemic stroke, including infusing the subject with a thrombolytic; and exposing the subject to a physical factor.

In Example 2, the method of Example 1, wherein the physical factor is low frequency vibration applied simultaneously with the infusion.

In Example 3, the method of Example 2, wherein the low frequency vibration is between about 0.5 Hz and about 120 Hz.

In Example 4, the method of Example 1, the physical factor is a countermeasure for barometric pressure, gravitational forces or acceleration applied with the infusion.

In Example 5, the method of Example 1, wherein the physical factor is low frequency vibration applied at a frequency between about 0.5 Hz and about 120 Hz.

In Example 6, the method of Example 1, wherein the physical factor is hypobaric environment.

In Example 7, the method of Example 1, wherein the physical factor is audible or non-audible noise.

In Example 8, the method of Example 1, wherein the infusion and exposure are performed via a device or program fitted to a hospital bed or gurney.

In Example 9, the method of Example 8, wherein the exposure is performed via a dedicated vibration stimulator at a frequency between about 0.5 Hz to about 120 Hz.

In Example 10, the method of Example 1, wherein the infusion and exposure is performed on the stretcher of a ground ambulance, an air ambulance or a mobile stroke unit.

In Example 11, the method of Example 1, wherein the infusion and exposure are applied to the subject for about an hour.

In Example 12, a method of enhancing thrombolysis to a subject in need thereof, comprising administering a thrombolytic and a low frequency vibration of about 0.5 Hz to about 120 Hz.

In Example 13, the method of Example 12, wherein the subject has an acute ischemic stroke.

In Example 14, the method of Example 12, wherein the administration occurs simultaneously.

In Example 15, the method of Example 14, wherein the low frequency vibration is between about 20 Hz and about 30 Hz.

In Example 16, the method of Example 12, wherein the administration is performed via a dedicated vibration stimulator.

In Example 17, a method for mitigating acute ischemic stroke in a subject, comprising providing a low frequency vibration simulator; and a pump and cannula; and administering a low frequency vibration of between about 0.5 Hz and about 120 Hz; and an infusion of at least one thrombolytic selected from the group consisting of tissue plasminogen activator, alteplase, reteplase, urokinase, streptokinase and tenecteplase.

In Example 18, the method of Example 17, wherein the administration occurs simultaneously.

In Example 19, the method of Example 17, wherein the administration occurs sequentially.

In Example 20, the method of Example 17, wherein the low frequency vibration is between about 20 Hz and about 30 Hz.

Other embodiments of these Examples include corresponding computer systems, apparatus, and computer programs recorded on one or more computer storage devices, each configured to perform the actions of the methods. Implementations of the described techniques and Examples may include hardware, a method or process, or computer software on a computer-accessible medium.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 7. Results of the main rtPA experiment in regard to (A) MiII infarct volume, (B) % "good" (0-2) outcomes in the Bederson Neurological scores, and (C) hyperacute BBB permeability on MiII.

DETAILED DESCRIPTION

Figure 1:
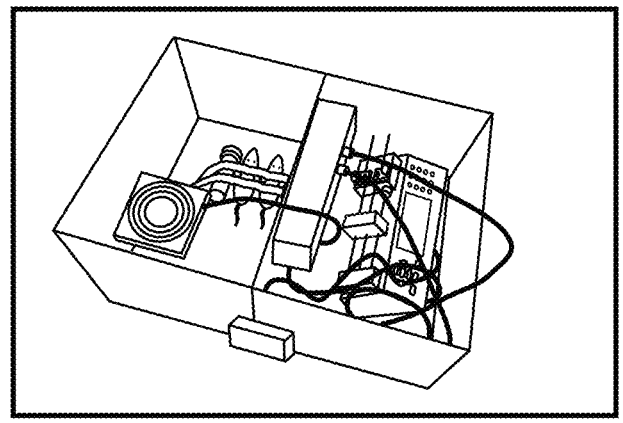
FIG. 1 depicts an exemplary implementation of an animal box having rtPA pumps, according to one Example.
Figure 2A:
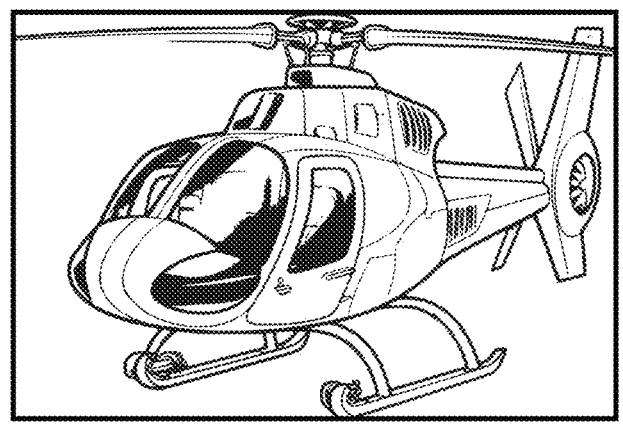
FIG. 2A depicts an exemplary helicopter for use in one Example.
Figure 2B:
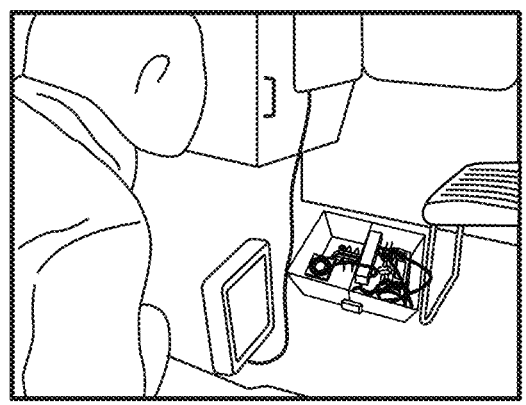
FIG. 2B depicts an animal box inside a helicopter, for use according to one Example.

The various embodiments disclosed or contemplated herein relate to devices, systems and methods for the treatment of patients in need thereof, including stroke patients. In various implementations, vibration or other physical forces are employed or dampened so as to be used as thrombolytic treatments for patient in need thereof.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to the target of administration, e.g., an animal. Thus, the subject of the herein disclosed methods can be a human, non-human primate, horse, pig, rabbit, dog, sheep, goat, cow, cat, guinea pig or rodent, or a mannequin that reproduces the human head and body consistency with an actual blood clot similar to the ones that occur in patients with stroke. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "subject" refers to the target of administration, e.g., an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more thrombosis disorders prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii)

inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with stroke" means having been subjected to a physical examination by a person of skill, for example, a physician, and found to have a condition that can be diagnosed or treated by a treatment that can treat or mitigate stroke or thrombosis. A subject having a stroke or thrombosis or the onset of a stroke or other thrombosis event may be identified using methods known in the art.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, administration to specific organs through invasion, intramuscular administration, intratumoral administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Intravenous tissue plasminogen activators (tPA) and recombinant tissue plasminogen activators (rtPAs) remain the only approved medical treatment for acute ischemic stroke, and with limited success. There is a critical need for additional interventions to further enhance the efficacy of rtPA. Patients with stroke in remote or congested areas typically receive the rtPA infusion while being evacuated by HEMS to a tertiary stroke centers (HEMS), known colloquially as "drip & ship". Those helicopter flights generate complex physical factors that have plausible effects on stroke and reperfusion that heretofore have been ignored. These factors include predominately low frequency vibrations (LFV), but also extreme noise, accelerations in three-axes, and rapid barometric changes. Importantly, any of these factors can be plausibly harmful or beneficial. It is therefore critical to understand the overall effects of HEMS-related physical factors, and LFV in particular. Mitigating any harmful effect could lead to optimization of those drip & ship HEMS transfers. But even more importantly, the identification of beneficial HEMS physical factors could lead to the development of interventions to improve patient outcomes in all care settings. Because, randomized studies of the effect of HEMS flights in stroke patients would be problematic logistically and ethically, we previously reported the feasibility of conducting translational animal research during actual helicopter flights. The present disclosure relates to the actual effect of helicopter flights, and the isolated effect of helicopter-like LFV, in a murine model of acute ischemic thromboembolic stroke.

In various implementations, physical forces or factors are applied and/or dampened to facilitate maximal or optimal thrombolytic effects. In alternate implementations, the method of enhancing thrombolysis to a patient in need thereof includes mitigating the effect of at least one harmful physical factor present during patient transportation. In yet further implementations, certain physical factors or forces are applied while others are dampened, as would be appreciated. As one non-limiting example, consistent vibration may be applied to the patient and noise and/or pressure effects—such as in a helicopter—may be dampened. Other combinations are of course possible and well within the scope of the present disclosure.

Various implementations comprise various devices and/or software constructed and arranged to facilitate such application or dampening of physical forces or factors. In certain implementations, the subjects are in need of thrombolytic treatments. Other implementations and treatment regimens are contemplated.

In certain implementations, a method of enhancing thrombolysis to a patient with acute ischemic stroke in need thereof is provided. In certain implementations, the patient has an acute ischemic stroke, though those of skill in the art will readily appreciate additional situations where thrombolysis is warranted. In various implementations, the method comprises exposing the patient to a simultaneous physical factor or force, such as vibration or pressure.

As such, these Examples establish that treatment protocols utilizing or administering a combination of LFV and rtPA to a subject in need thereof can improve the outcomes related to acute ischemic stroke. In various implementations, the administration of LFV and rtPA can be simultaneous, such as over the course of about an hour, although it is readily appreciated that alternate implementations can be of shorter durations such as one or more minutes to longer durations lasting about several hours. That is, the administration can be anywhere from about a minute to several hours long.

Various implementations of the method utilize vibrations as a physical factor. Certain implementations use vibrations of about 0.5 Hz, about 20 Hz to about 30 Hz or about 60 Hz or less applied constantly or intermittently over seconds, minutes or hours, though other frequencies and durations are possible. Further implementations utilize frequencies of about 61 Hz or more. Additional implementations employ higher-frequency vibrations of up to about 100 Hz, up to about 120 Hz, up to about 200 Hz or, in certain implementations even higher. These and alternate implementations may apply barometric pressure, gravitational forces, noise and/or acceleration, and in certain implementations as countermeasures. Other forces or physical factors are also contemplated.

In certain implementations, the administration is performed via a device or program constructed and arranged to be fitted to a hospital bed. In certain of these implementations, the administration is performed via a dedicated vibration stimulator or via a device constructed and arranged to be fitted to a gurney.

In certain implementations, the co-administration of a physical force such as LFV and a thrombolytic such as rtPA is performed to a subject in need thereof to synergistic effect. The co-administration can be sequential in either direction, that is the subject can be infused with thrombolytic prior to physical force administration, such that the infusion begins at a time prior to the onset of administration of the physical force or vice versa. In further alternate implementations, the physical force can be initiated prior to infusion. In various implementations the administrations overlap with one another, while in additional implementations the infusion and the physical force administration are performed purely sequentially—the administration need not contemporaneously overlap, for example infusion may conclude at about the time that the physical force administration is initiated or vice versa.

In various implementations, the physical force can be low frequency vibration or other physical forces such as noise, accelerations in three-axes, and rapid barometric changes. In alternate implementations, certain of these forces may be applied as countermeasures to prevent adverse environmental conditions.

In various implementations, a variety of tPAs/rtPAs or other thrombolytics known and understood in the art can be combined with the LFV. For example, certain non-limiting examples include Activase®, Abbokinase®, Cathflo® Activase®, Kinlytic®, Retavase®, Strepase®, TNKase®, alteplase, anistreplase, reteplase, urokinase, streptokinase and tenecteplase. Those of skill in art would readily appreciate and understand the various alternatives.

Infusion of the thrombolytic can be an effective dose of tPA (rtPA) or other thrombolytic and can be performed at a range of concentrations. Certain non-limiting examples include the administration of Cathflo® Activase® at 0.9 mg/kg, or any range between about 0.05 mg/kg to 1.25 mg/kg, up to a maximum of 90 mg, 100 mg, 125 mg or more, as would be readily appreciated, depending on the thrombolytic. It is readily appreciated that other common dosages of alternate thrombolytics can be applied as would be readily appreciated by those of skill in the art familiar with the dosing. Certain non-limiting examples include TNKase® (tenecteplase) administered at from about 20 mg to about 50 mg, Activase® (alteplase) administered at from about 10 mg to about 200 mg, such as 100 mg over 3 hours, Eminase (anistreplase) administered from of about 10-50 units over 2-5 minutes, Retavase® (reteplase) administered at about 10 or more units per bolus, urokinase dosages of around 3,000-9,000 IU/minute for about 2 hours or for a total of about 100,000-900,000 IU total, streptokinase administered at about 100,000-200,000 units followed by maintenance infusions, and the like. While these dosages are provided herein, it is readily appreciated that the dosing regimens of each of the various thrombolytics can be varied according to the routine experimentation and understanding of those of skill in the art in view of the present disclosure.

As discussed herein, the physical force administration can be low frequency vibration (LFV) performed at a variety of frequencies, such as those from about 0.5 Hz to about 120 Hz. In further administrations the LFV is applied at about 20 Hz to about 30 Hz. Further administrations are performed at around 60 Hz. Additional administrations are performed at more than 120 Hz.

In certain additional implementations, these methods are performed in a hospital bed, while in others the method is performed via the stretcher of a ground or air ambulance to amplify or supplement the vibration present in those transportation systems. Implementations of the described techniques may include hardware, a method or process, or computer software on a computer-accessible medium.

A novel experimental animal model to accurately replicate the scenario of stroke reperfusion ("drip & ship") during HEMS as a means of assessing the value of vibrations, including at various frequencies, and other helicopter related forces on stroke outcomes.

EXPERIMENTAL EXAMPLES

The following examples are put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

Figure 3:
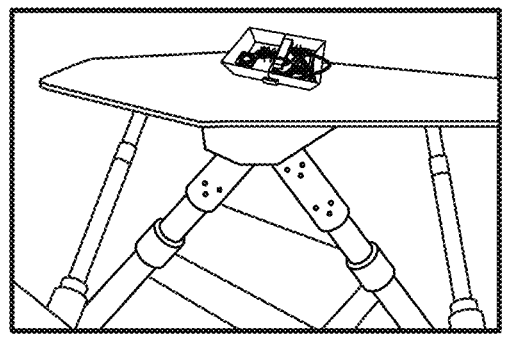
FIG. 3 depicts a vibration simulator, according to an Example.

FIGS. 1-5 depict the components and results of the Example. FIG. 1 depicts an exemplary implementation of an animal box having rtPA pumps, and FIG. 2A depicts an exemplary helicopter for use in the study, with FIG. 2B depicting the animal box inside the helicopter. FIG. 3 depicts a vibration simulator.

Methods. In this Example, a drip & ship model was developed using middle cerebral artery occlusion (MCAO) with autologous clots in mice and an Mi2 helicopter adapted for animal research. Since vibration is one of the most salient physical components in helicopter emergent medical services (HEMS) transportation, the Example isolated this factor with a simulator for mechanistic investigation. The vibratory signature during HEMS was recorded in-flight using accelerometers and then recapitulated in a six-degree-of-freedom man-rated Moog-FCS motion platform in the laboratory. This example evaluated two approaches (simultaneous vs. sequential) to expose mice with MCAO to the three different settings (helicopter/simulator/ground) in order to find the most optimal methodologically.

Results

Figure 4:
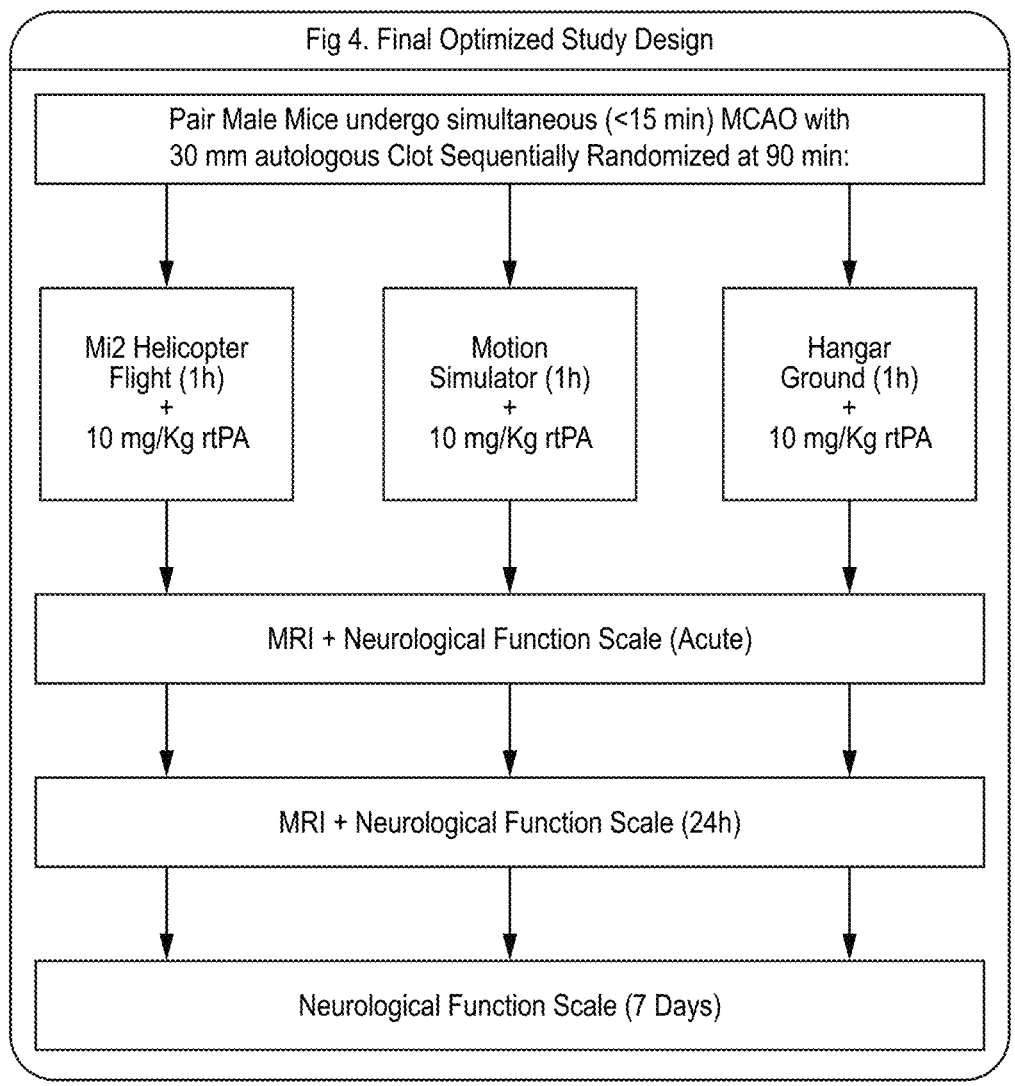
FIG. 4 is an overview schematic and flow chart of an Example design.

FIG. 4 depicts the overview of the Example methods. In this Example, clot length of 30 mm and 90 min of rTPA initiation post MCAO achieved significant infarctions while minimizing periprocedural mortality. Two MCAOs were the maximum capable of achieving occlusion times <15 minutes apart. In the implementation of FIG. 4, a in order to maintain MCAO to rtPA times close to 90 minutes, a sequential exposure to the three settings (helicopter/simulator/ground) was established with 2 mice each. Randomly assigned exposures lasted for 1 hour, and occurred at the same time as the rtPA exposure. The three exposures were 2 hours apart to minimize the effect of atmospheric variations. The animal MRI facility was coordinated to acutely scan the brain of the animals after the three exposures to minimize the effect of early mortality in infarct outcome determination.

Accordingly, this Example developed an animal model to study the effects of HEMS on rtPA/reperfusion. An ongoing experiment measuring infarction volume and clinical outcomes will determine the need to maintain an actual HEMS for future experiments, or whether a laboratory simulator will suffice.

Example 2

Figure 5:
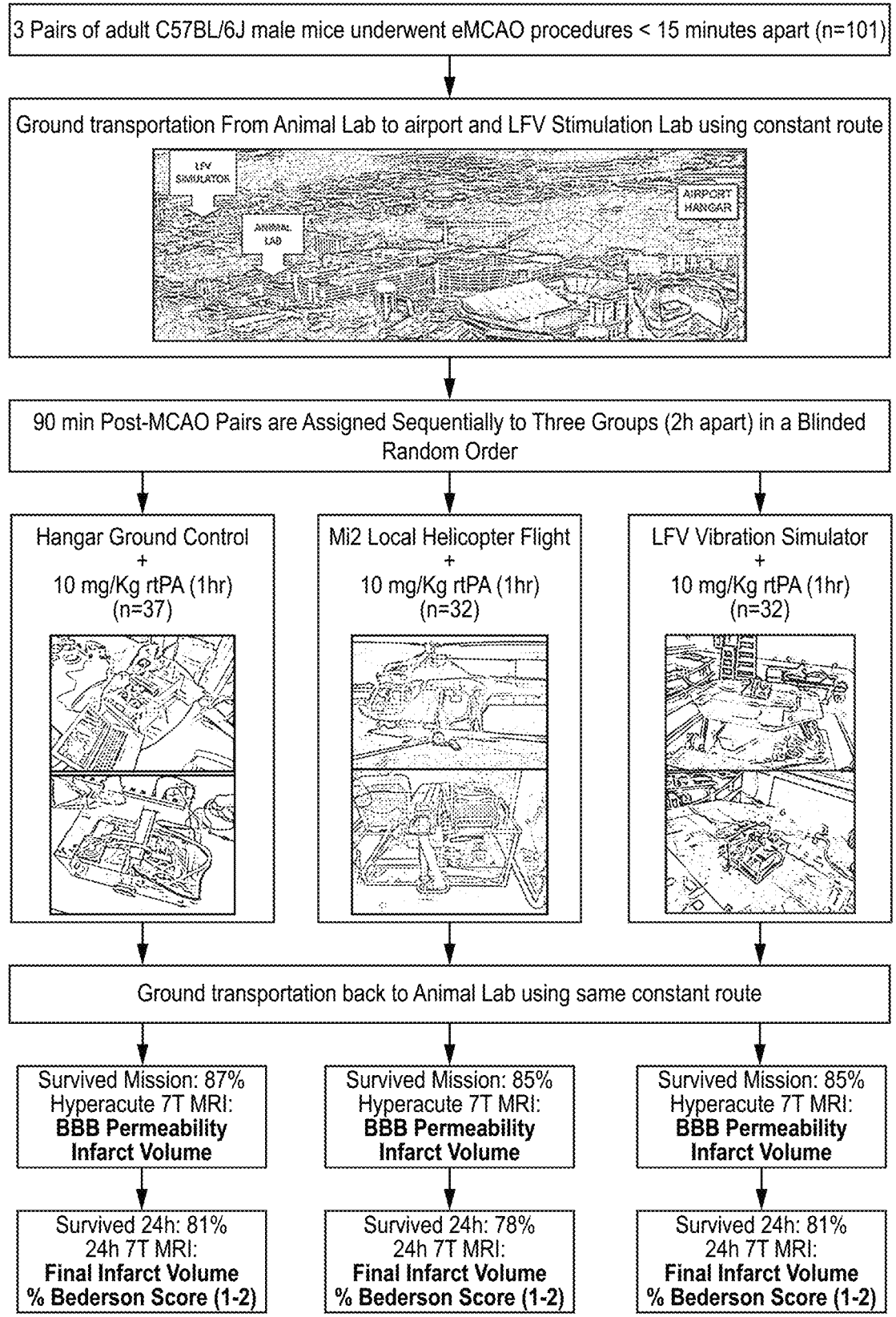
FIG. 5 is another overview schematic and flow chart of an Example design.

This was a prospective randomized controlled study conducted between February 2018 and February 2019. Mice with a middle cerebral artery autologous thromboembolic occlusion (eMCAO) were randomized to receive rtPA 90 minutes later in three different settings: 1) a standardized actual helicopter flight, 2) A motion platform simulator that reproduced the LFV signature of the helicopter without the other flight physical factors, and 3) a ground control (FIG. 5). Main outcome measures were residual infarct size on MM, and % of good neurological outcomes. Hyperacute blood brain barrier (BBB) permeability was a secondary outcome. Pre-scheduled missions proceeded to surgery only if weather conditions permitted, and the animal laboratory was simultaneously available along with the helicopter, vibration simulator and neuroimaging teams and equipment. A subsequent study using saline was planned in case of positive results to explore possible interactions with rtPA.

Thromboembolic Occlusion.

We previously optimized the murine model in regards to maximal number of simultaneous surgeries and clot size, and determined that two simultaneous surgeries and a 30 mm clot achieved eMCAO less than 15 minutes apart with adequate infarction size. Pairs of 10-14 week old C57BL/6J male mice underwent the method described by Overgaard et al with slight modification. Animals were anesthetized with 1-1.5% isoflurane during the surgery. The catheter containing a single 30 mm fibrin-rich clot was then introduced into the external carotid artery and advanced to the internal carotid artery. After embolization, the catheter was removed and the external carotid artery was blocked by cauterization. Laser Doppler flow monitoring (Perimed Instruments, Stockholm, Sweden) was used to confirm the induction of brain hypoperfusion. The body temperature of the mouse was maintained at 37±1 C° during the entire procedure. Buprenorphine (0.1 mg/kg, SC) was administered as an analgesic agent every 6-12 hours for 48 hours post-surgery. The right jugular vein was cannulated and connected to the pump for the administration of rtPA (Cathflo, Genentech), 10 mg/kg, 10% volume by bolus and remaining slow infusion for 45 minutes, or same volume of saline, 90 minutes post-embolization.

Experimental Group Assignment.

In each day of the experiment, three pairs of mice were sequentially assigned to receive the three exposures (helicopter, LFV simulator or ground control) in a random order 2$h$ apart (FIG. 5). Following surgery, each pair of mice was protected by conical restraints and placed on the floor of a customized 0.6 mm thick acrylic Plexiglas box (48.5×20.5× 34.6 cm) equipped with accelerometers, and pre-programmed syringe pumps attached to IV lines (FIG. 5). The surgeon, blinded to randomization status, handed the animal box to an unblinded investigator (ECL) who transported it to the assigned exposure in an Institutional Animal Care and Use Committee (IACUC)-approved ground vehicle (FIG. 5). The driving was kept constant for the three groups by using a triangular route of 5 miles total (animal lab-LFV simulator-airport-animal lab). In all three exposures, the IV rtPA pumps were manually started exactly 90 minutes from the half-way point between the two mice eMCAO times. The box was equipped with fan, air cooling unit, heating pads, which were manually operated as needed aiming for a target of 25 C°. All operational times and atmospheric variables were recorded.

Flight.

The flight exposure consisted of a soviet-era Mi2 HEMS/military dual turbine (298 kW, 400 sHP) helicopter certified and instrumented as an airborne laboratory, as is shown in FIG. 5. The animal box was secured to the floor of the helicopter in a consistent way for reproducibility of the LFV exposure. Engine start time always coordinated with IV pump initiation. A 1-hour local standardized flight was conducted in visual meteorological conditions at an altitude of 1000 feet (309 meters) above ground in and out of Iowa City Municipal Airport, Iowa (KIOW), following a triangular path with Muscatine, Iowa (KMUT) and Washington, Iowa (KAWG) as waypoints (total distance: 71.3 nm, 132 Km).

LFV Stimulation.

Figure 6A:
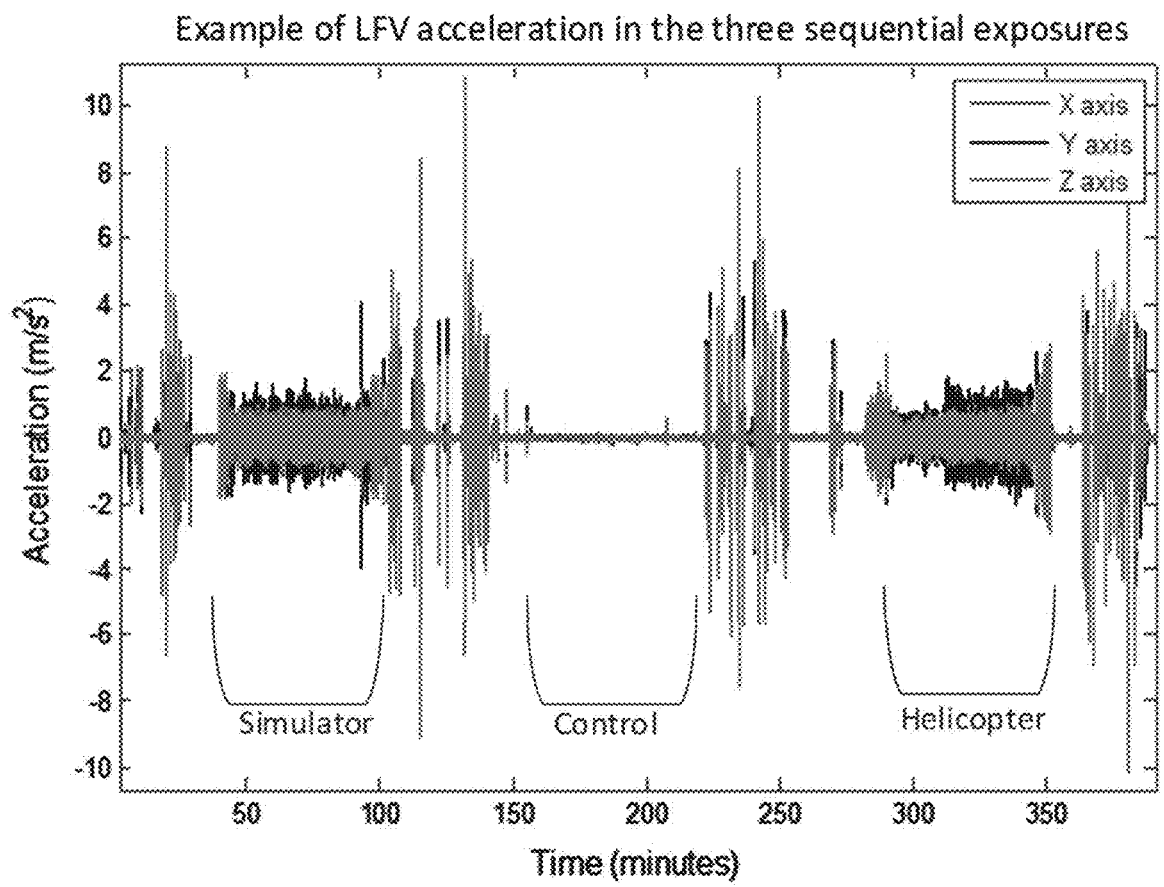
FIG. 6. (A) Time based LFV profile of a typical experiment with the three sequential missions (Simulator-Control-Flight). Colors indicate X Y and Z axes (fore-aft, lateral, vertical). Handling and driving seen at around 10 minutes (brief spikes), LFV simulator motion 45-105 minutes, then handling and driving (brief spikes), control setting from 155-215, handling and driving (brief spikes), then Mi2 flight 280-350, followed by handling and driving (brief spikes). (B) Average mean LFV vibration (95% CI) by frequency bands between the LFV simulator and Helicopter flights.

The LFV simulation exposure (also 1 hour) consisted of a modified six-degree-of-freedom man-rated Moog-FCS motion platform simulator capable of consistent reproduction motions up to 30 Hz. A tactile transducer was added to the animal box to extend the vibration to the 60 Hz range (FIG. 5). This simulator reproduced with fidelity the LFV signature of a Mi2 flight that was previously recorded with accelerometers (X16, Gulf Coast Data Concepts) in three directional axes, and which involved multiple waveforms in the 1-120 Hz range (FIG. 6). Simulated engine start was adjusted to always coincide with IV pump initiation.

The animal box assigned to ground control received the IV infusion in an office inside the hangar of the research facility at KIOW.

Blinded MRI and Clinical Outcome Analyses.

After each exposure, animals were returned to the laboratory where Mills were immediately performed, per established protocol, to analyze acute changes in BBB permeability expressed as percentage of Gd-DTPA enhancement within the ischemic lesion. Hyperacute infarction size was also analyzed to minimize loss of data from animal death.

The MRI was repeated at 24 h and used for a more precise infarction determination. Animals were anesthetized with isoflurane (2.5% induction, 1.2% maintenance) and placed in the bore of the 7.0 Tesla Mill (Agilent Technologies Inc., Santa Clara, Calif., USA) with a two-channel receive-only surface coil.

Image Collection and Processing.

Following scout scans, high-resolution images were acquired with a 9-minute T2-weighted 2D fast spin-echo sequence oriented coronally. Imaging parameters included TR/TE=6380 ms/83 ms, echo train length of 12, and 7 signal averages to achieve voxel resolution 0.10 mm×0.10 mm×0.50 mm with no gaps. This was followed by intraperitoneal injection of gadobuterol (Gadavist, Bayer HealthCare) at a dose of 0.3 mmol/kg and subsequent multiple 3D gradient echo acquisitions in the same coronal plane (TR/TE=25/3 ms, flip angle 30°, resolution 0.1 mm×0.1 mm×0.25 mm, 3 minutes per scan) acquired over 25 minutes. The area of infarction was quantified by a blinded operator using NIH Image J software by outlining the zone with abnormally T2 hyperintense regions in each brain slice, and total infarct volume was obtained by summation of the infarcted areas multiplied by the slice thickness. To correct for brain swelling due to edema after ischemia, the corrected total infarct volume (%) was calculated. The BBB permeability was quantified by a blinded operator using NIH Image J software by outlining the zone with abnormally hyperintense regions in each brain slice, and total BBB leakage volume was obtained by summation of the hyperintense areas multiplied by the slice thickness. The Bederson scale, which is a global neurological assessment in experimental models, was used to by a blinded observer to measure neurological impairment. A score of 0-2 was categorized as "good".

Statistical Consideration and Sample Size.

The differences in the effect of the three exposures of interest (ground control, helicopter, LFV simulator) on the outcome measures was assessed using linear mixed model analysis for infarction, and BBB permeability. and by logistic regression fitted by generalized estimating equations (GEE) method for favorable neurological outcome (0-2 of 4 point scale). The p-values for pairwise comparison between exposures were adjusted using Tukey-Kramer method. The models were expanded to include covariates to account for potential effect of confounders, which included time to rtPA infusion start, outside temperature, barometric pressure, dew point, total vibration during exposure, and vibration during ground transportation. Based on infarction size data from our pilot study, assuming an infarct difference of 33 and standard deviation of 95, we determined that a sample size of at least 25 per group would detect a 25% reduction between groups with 0.80 power at a significance level of 0.05. All experimental procedures were approved by the University of IACUC.

Figure 6B:
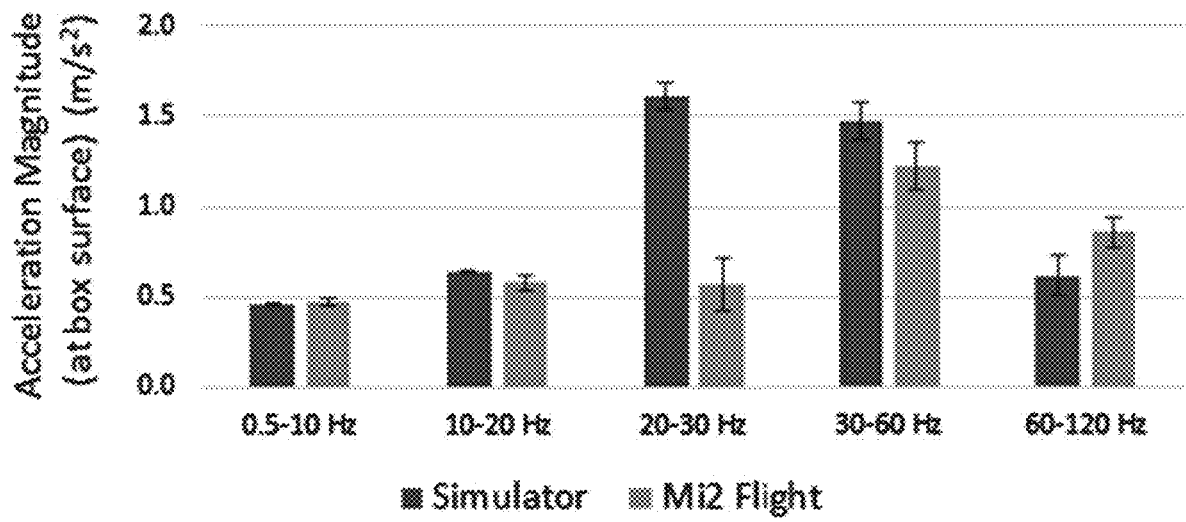

FIG. 5 shows a CONSORT-style study diagram. One hundred and one mice were included. The 24 h mortality of 19-22% was the same in all three groups, and consistent with the expected perioperative mortality of the thromboembolic model FIG. 6B shows the box accelerometer amplitude measurements between the helicopter flight and the LFV simulator by frequency band. The two groups delivered comparable LFV energy, with the exception of the 20-30 Hz band which was overrepresented in the simulator group. Main results of the study are shown in FIG. 7.

The mice in the helicopter group did not show a reduction in infarct volume (47.8 vs. 54.9 mm$^3$, difference of −7.1; 95% CI: −24.8, 10.5; p=0.58) or better neurological outcomes when compared to the control group (37 vs. 28%, odds ratio of 1.52; 95% CI: 0.43, 5.30; p=0.71). On the other hand, mice assigned to the LFV simulator had significantly smaller infarction volumes than ground controls (31.6 vs. 54.9 mm$^3$, difference of −23.4; 95% CI: −40.8, −6.0; p=0.007), and also a significantly higher percentage of good neurological outcomes (87 vs. 28%, odds ratio of 15.08; 95% CI: 3.22, 70.60; p=0.0001). The adjusted linear mixed model to account for confounding effects of the covariates with respect to infarct volume, continued to show a significant effect of group exposure assignment (p=0.027). There was no significant difference in blood-brain barrier (BBB) permeability between the helicopter or ground LFV simulator, compared to controls (2.45, 3.02 vs. 4.82 mm$^3$; difference of −2.37; 95% CI: −4.03, 0.84; p=0.14 for helicopter, and difference of −1.80; 95% CI: −3.74, 1.96; p=0.36 for simulator).

Figure 8A:
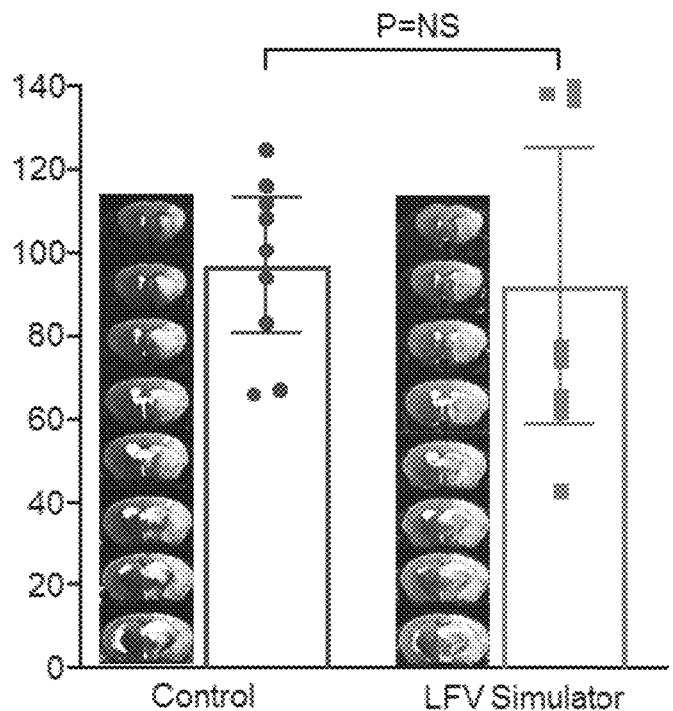
FIG. 8. Results of the subsequent exploratory, saline-only, Example in regard to (A) MM infarct volume, (B) % "good" (0-2) outcomes in the Bederson Neurological scores, and (C) hyperacute BBB permeability on MM.
Figure 8B:
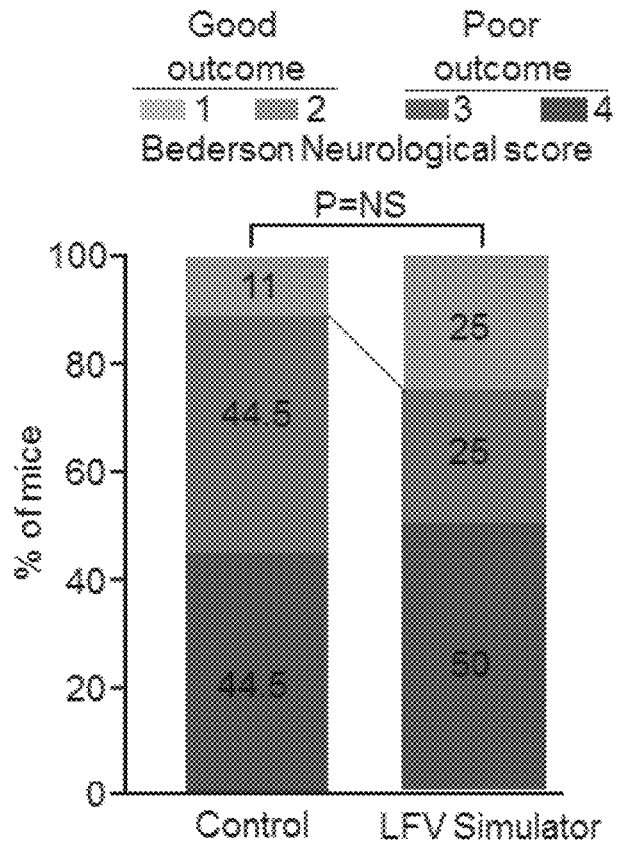
Figure 8C:
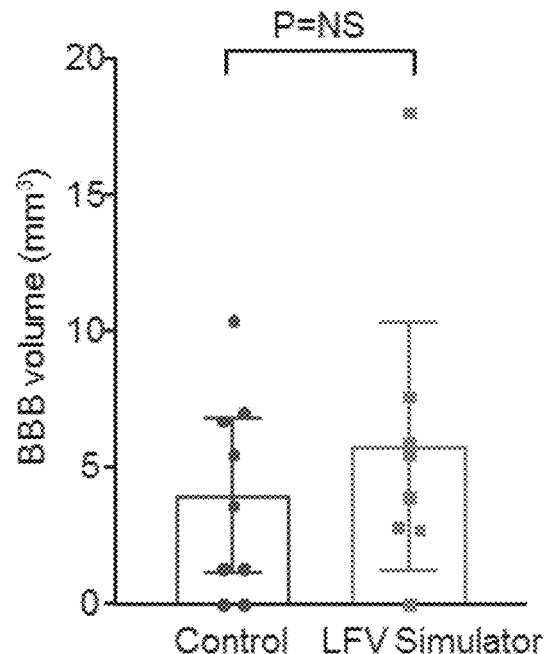

A subsequent similar study using saline was conducted after these positive results to determine whether LFV alone had an effect on stroke outcomes independently of rtPA. Here, we conducted 4 missions comparing LFV simulator and control using saline (total n=18) (FIG. 8), and found no differences between the LFV simulator group and control group with respect to infarct size (80.9 vs. 95.3, difference of −4.4; 95% CI: −58.3, 49.6; p=0.81) or good neurological outcomes (25 vs. 11%, odds ratio of 2.65; 95% CI: 0.53, 13.29; p=0.24).

Discussion

The disclosed Examples are the first report of a synergistic effect between a replicated helicopter-like LFV on the ground and rtPA thrombolysis on stroke outcomes. The magnitude of this synergistic effect was substantial, with approximately half the infarct volume and triple the percentage of good neurological outcomes compared to rtPA alone.

These Examples involved large samples with rigorous methodology to eliminate bias establish that LFV provides a supplemental treatment strategy for patients with stroke undergoing thrombolysis, such as in addition to rtPA. Although the concept of enhancing rtPA thrombolysis with physical energy has also been proposed with ultrasound, unlike the present Examples large studies with ultrasound have failed to show any effect.

Further, unlike transcranial focused ultrasound, LFV can be achieved in clinical settings, such as via devices and programs implemented in hospital beds, on gurneys and the like. For example, LFV is omnidirectional and does not require sophisticated equipment or human expertise necessary to deliver focused energy. Instead, LFV can be delivered in hospital and ambulance patient beds. Moreover, LFV is considered safe and does not raise concerns of brain cavitation, as demonstrated herein. The lack of effect on BBB permeability is also reassuring, as would be appreciated and is shown in FIG. 7C.

These Example results are also consistent with studies showing LFV-mediated acceleration of reperfusion in in-vitro experiments. LFV has been previously proposed to influence blood flow through convective currents and velocity shifts, which could conceivably facilitate clot erosion and rtPA exposure, nitric oxide release by blood vessels, or increased rtPA levels. Notably, we did not observe an independent effect of LFV in the Examples, suggesting that the synergism between LFV and rtPA is important to enhance outcomes.

Surprisingly, we did not observe the same benefit in mice exposed to the actual helicopter flights, as shown for example in FIG. 7. While there was a possible benefit in the helicopter group compared with ground, the difference was not significant. The LFV energy that was delivered in the helicopter was comparable to the one generated in the simulator, with the notable exception of the 20-30 Hz band. This 20-30 Hz frequency band was unexpectedly delivered with larger intensity in the LFV simulator, either due to unforeseen resonance in the platform/speakers or sampling issues with the flight used to elicit the original LFV signature. Therefore, the difference in outcomes between the helicopter and the LFV simulator groups could be related to a possible causative effect of the 20-30 Hz frequency band. This was suggested by exploratory logistic analyses using the different frequency bands where a significant association of 20-30 Hz intensity with infarct volume and neurological outcome was observed (results not shown).

Retrospective studies in patients with stroke transported by helicopter have shown mixed clinical outcomes, ranging from no effect to a hint of potential benefit, but there is variability in the LFV signature between different helicopter ambulances used in clinical care. Still, we cannot exclude with this study a negating effect of other as-yet unidentified physical factors present in flight.

Importantly, the potential negative effect of helicopter transportation on the pharmacological integrity of rtPA has been specifically ruled-out. The lack of significance of outside temperature and other atmospheric variables in the multivariate model makes temperature an unlikely confounding factor. However, other factors present in helicopter flight do present plausible negative effects. For example, rapid barometric reductions could result in hypoxia in the ischemic penumbra, and accelerations in three axes, as well as extreme noise (105 db), could also negatively influence the outcome. Future work will focus on measuring these factors in helicopter flights and recapitulating them in the ground scenario in order to determine their independent effect.

While small vibratory exposure received during ground transportation has the potential to effect the study, it was believed that this factor was negligible given the duration of the ground transportation (FIG. 5) and consistency between the three groups. Furthermore, this ground transportation acceleration was measured (FIG. 6), and it did not confound the results as shown in the adjusted multivariate analysis.

There are human translational concerns regarding stroke models, including scaling issues. The use of an animal stroke model was needed, however, to rigorously address our question, as it would be unethical to randomize patients with acute stroke to different transport modalities and rtPA/saline at pre-specified points of time. The lack of any negative effects of flights on stroke outcomes, including no increase in BBB permeability as previously suggested, supports the safety of neuroprotection delivered during helicopter transport.

In summary, the disclosed Examples have identified a synergistic effect between recapitulation of the LFV signature of a helicopter flight on the ground with rtPA treatment with respect to reperfusion outcomes in a mouse stroke model. This novel finding forms the basis for a supplemental intervention that can improve patient care.

Although the disclosure has been described with reference to preferred embodiments, persons skilled in the art will recognize that changes may be made in form and detail without departing from the spirit and scope of the disclosed apparatus, systems and methods.

What is claimed is:

1. A method of enhancing thrombolysis in a subject with acute ischemic stroke, comprising:
   infusing the subject with a thrombolytic, the subject positioned upon a support surface supporting the entire subject; and
   applying low frequency vibration of between about 0.5 Hz and about 120 Hz to the subject solely with the support surface.

2. The method of claim 1, wherein the low frequency vibration is applied simultaneously with the infusion.

3. The method of claim 1, further comprising dampening one or more physical factors during the infusion.

4. The method of claim 1, wherein the thrombolytic is a recombinant tissue plasminogen activator.

5. The method of claim 1, further comprising exposing the subject to a hypobaric environment.

6. The method of claim 1, further comprising exposing the subject to audible or non-audible noise.

7. The method of claim 1, wherein the support surface comprises a hospital bed or gurney.

8. The method of claim 7, wherein the support surface comprises a motion platform.

9. The method of claim 1, wherein the support surface comprises a stretcher of a ground ambulance, an air ambulance or a mobile stroke unit.

10. The method of claim 1, wherein the infusion and low frequency vibration are applied to the subject for about an hour.

11. The method of claim 1, wherein applying the low frequency vibration to the subject via the support surface comprises vibrating the support surface with a dedicated vibration stimulator fitted to the support surface.

12. A method of enhancing thrombolysis to a subject in need thereof, comprising administering:
   a) a thrombolytic; and
   b) low frequency vibration of between about 0.5 Hz to about 120 Hz to the subject via a dedicated vibration device comprising a motion platform positioned under and supporting the entire subject.

13. The method of claim 12, wherein the subject has an acute ischemic stroke.

14. The method of claim 12, wherein the administration occurs simultaneously.

15. The method of claim 14, wherein the thrombolytic is a recombinant tissue plasminogen activator.

16. A method for mitigating acute ischemic stroke in a subject, comprising:
   providing:
      i) a vibration device comprising a motion platform; and
      ii) a pump and cannula;
   supporting the entire subject with the motion platform; and
   administering:
      i) low frequency vibration of between about 0.5 Hz and about 120 Hz via the motion platform to the subject positioned upon the motion platform; and
      ii) an infusion of at least one thrombolytic selected from the group consisting of tissue plasminogen activator, alteplase, reteplase, urokinase, streptokinase and tenecteplase.

17. The method of claim 16, wherein the administration occurs simultaneously.

18. The method of claim 16, wherein the administration occurs sequentially.

19. The method of claim 16, wherein the low frequency vibration is between about 20 Hz and about 30 Hz.

* * * * *